United States Patent [19]

Blumberg et al.

[11] Patent Number: 5,763,215
[45] Date of Patent: Jun. 9, 1998

[54] METHOD OF REMOVING N-TERMINAL AMINO ACID RESIDUES FROM EUCARYOTIC POLYPEPTIDE ANALOGS AND POLYPEPTIDES PRODUCED THEREBY

[75] Inventors: Shmaryahu Blumberg, Rishon Le-Zion; Daniella Ben-Meir, Ramat-Gan, both of Israel

[73] Assignee: Bio-Technology General Corporation, Iselin, N.J.

[21] Appl. No.: 400,544

[22] Filed: Mar. 8, 1995

Related U.S. Application Data

[63] Continuation of Ser. No. 243,045, May 16, 1994, abandoned, which is a continuation of Ser. No. 96,067, Jul. 22, 1993, abandoned, which is a continuation of Ser. No. 873,876, Apr. 22, 1992, abandoned, which is a continuation of Ser. No. 445,911, Dec. 4, 1989, abandoned, which is a continuation of Ser. No. 770,692, Aug. 29, 1985, abandoned, which is a continuation-in-part of Ser. No. 641,488, Aug. 16, 1984, abandoned.

[30] Foreign Application Priority Data

Aug. 15, 1985 [IL] Israel ............................................ 76107

[51] Int. Cl.⁶ .............................. C12P 21/02; C12N 9/48; C12N 15/01; C12N 15/09
[52] U.S. Cl. ................ 435/69.1; 435/68.1; 435/172.212
[58] Field of Search ................................. 435/68.1, 69.1, 435/172.3, 212

[56] References Cited

U.S. PATENT DOCUMENTS

| 4,543,329 | 9/1985 | Daum et al. ............................ 435/69.1 |
| 4,667,017 | 5/1987 | Ishida .................................... 530/402 |
| 5,633,352 | 5/1997 | Dalboge et al. ......................... 530/399 |

FOREIGN PATENT DOCUMENTS 8402351  6/1984  WIPO.

OTHER PUBLICATIONS

Wilkes et al Eur. I. Biochem 1973 pp. 459–466.
Harris Genetic Engineering 4 1983 pp. 131–138.
Vosbeck et al. J. Biol. Chem. (1975) 250 (10) pp. 3981–3987.
Roncari et al Int. J. Prot. Res. (1969) 191) pp. 45–61.
Seeburg et al DNA (1983) 2(1) PP. 37–45.
McLean et al J. Biol. Chem. (1984) 259(10) 6498–504.

*Primary Examiner*—Nancy Degen
*Attorney, Agent, or Firm*—John P. White

[57] ABSTRACT

A method of sequentially removing one or more N-terminal amino acid residues from an analog of a eucaryotic polypeptide synthesized in a foreign host, comprises contacting the eucaryotic polypeptide analog with aminopeptidase under suitable conditions permitting sequential removal of N-terminal amino acid residues, where the polypeptide analog contains an amino acid residue or sequence of residues which blocks the action of an aminopeptidase located at a position other than the N-terminal end of the polypeptide analog. A specific embodiment of the invention concerns removing both an N-terminal methionine residue and its adjacent Leucine residue from a growth hormone analog produced in bacteria by contacting the growth hormone analog with Aeromonas aminopeptidase under suitable conditions permitting removal of the N-terminal methionine and Leucine residues. The invention also concerns eucaryotic polypeptide analogs produced in accordance with the methods of the invention.

3 Claims, 2 Drawing Sheets

METHOD OF REMOVING N-TERMINAL AMINO ACID RESIDUES FROM EUCARYOTIC POLYPEPTIDE ANALOGS AND POLYPEPTIDES PRODUCED THEREBY

This application is a continuation of U.S. application Ser. No. 08/243,045, filed May 16, 1994, now abandoned; which is a continuation of U.S. application Ser. No. 08/096,067, filed Jul. 22, 1993, now abandoned; which is a continuation of U.S. application Ser. No. 07/873,876, filed Apr. 22, 1992, now abandoned; which is a continuation of U.S. application Ser. No. 07/445,911, filed Dec. 4, 1989, now abandoned; which is a continuation of U.S. application Ser. No. 06/770,692, filed Aug. 29, 1985, now abandoned; which was a continuation-in-part of U.S. application Ser. No. 06/641,488, filed Aug. 16, 1984, now abandoned.

BACKGROUND OF THE INVENTION

Recombinant DNA technology permits large scale production of eucaryotic proteins in bacteria. However, the proteins so produced, are frequently characterized by the addition of an extra methionine residue at their N-terminus. This occurs because translation is always initiated at the AUG codon which codes for methionine. In procaryotes, the N-terminal methionine is frequently enzymatically removed. However, it appears that this is not the case for many eucaryotic proteins produced in bacteria. Possibly this is due to the fact that the proteins are massively overproduced and thus overwhelm the bacteria's processing capabilities. Another possible explanation is that the bacterial processing enzymes do not recognize the foreign eucaryotic proteins as their substrates.

In eucaryotes, mature proteins often lack an N-terminal methionine because they have undergone extensive processing by both endopeptidases and exopeptidases, during transport from the site of synthesis to their final location.

As the presence of an N-terminal methionine on eucaryotic proteins may cause an immune reaction when administered to eucaryotes, it would be desirable to process eucaryotic proteins produced in bacteria to remove the N-terminal methionine, thus producing the mature eucaryotic protein. Most available aminopeptidases are zinc metalloenzymes. They are comprised of several subunits and have very high molecular weights. (For a review see Delange and Smith, The Enzymes, 3rd edition, P. D. Boyer ed., 1971, vol. 3, pp. 81–118). Thus, leucine aminopeptidases from pig kidney and from bovine lens have molecular weights of 255,000 and 320,000, respectively. Although the exact role of these enzymes is not known, it is likely that such high molecular weight enzymes predominantly act on peptides. We demonstrate that one such leucine aminopeptidase is incapable of selectively removing the N-terminal methionine from methionyl-human growth hormone (Met-hGH). Some mammalian brain aminopeptidases capable of acting on low molecular weight peptides are either membrane bound or soluble enzymes, the latter having molecular weights of approximately 100,000. These enzymes often contain SH groups in addition to the essential metal atom and they are extremely unstable. All these enzymes seem to be of a rather little practical value for the "processing" of methionyl-polypeptide derivatives to mature polypeptides.

On the other hand, two microbial aminopeptidases that have been described in the literature with molecular weights of about 30,000 are promising candidates for the "processing" of met-polypeptides. The two enzymes are fairly thermostable as well as stable and optimally active at alkaline pH. The aminopeptidases most suitable for processing of Met-polypeptides are Aeromonas proteolytica aminopeptidase and Streptomyces griseus aminopeptidase.

Aeromonas aminopeptidase has been purified and characterized by Prescott and Wilkes [Methods in Enzymology 46:530–543 (1976)], and Wilkes et al., [Eur. J. Biochem. 34:459–466 (1973)]. Although they appear to demonstrate liberation of amino acids from the N-terminus of several polypeptides and proteins, there is no demonstration of the removal of just N-terminal methionine from proteins. Removal of N-terminal methionine is demonstrated for an oligopeptide of 11 residues; however, many other residues are also removed, in addition to the methionine. Furthermore, there is no demonstration of the activity of the enzyme on non-denatured hormones of a molecular weight greater than 10,000. There is also no indication whether the reactions carried out by Wilkes and Prescott are quantitative. Also, while the paper indicates several "stop signals" for the aminopeptidase, there is no indication that the stop signals Asp or X-Pro, where X is any amino acid except for proline, are also stop signals when the enzyme is reacted with proteins. Furthermore, preliminary results indicate that not all proteins are susceptible to attack by Aeromonas proteolytica aminopeptidase. It appears that mature eucaryotic proteins are "locked" into a conformation such that the N-terminus is inaccessible to the aminopeptidase. However, the methionyl form of the eucaryotic protein has a methionine which is susceptible to removal by the aminopeptidase. Similarly eucaryotic protein derivatives containing several additional amino acids at their N-terminus, will also be susceptible to removal by the same enzyme. We have discovered that Aeromonas aminopeptidase is capable of removing the N-terminal methionine from Met-human growth hormone (Met-hGH) and from methionine—Asp-Gln-bovine growth hormone (Met-Asp-Gln-bGH). We have also demonstrated that Aeromonas aminopeptidase is capable of removing the N-terminal methionine and its adjacent leucine from Met-Leu-hGH. The reaction is quantitative and there is no other degradation of the proteins.

SUMMARY OF THE INVENTION

A method of sequentially removing the N-terminal amino acid residues from an analog of a eucaryotic polypeptide synthesized in a foreign host comprises contacting the eucaryotic polypeptide analog with the aminopeptidase under suitable conditions permitting sequential removal of N-terminal amino acid residues. The polypeptide analog contains an amino acid residue or sequence of residues which stops the action of an aminopeptidase located at a position other than the N-terminal end of the polypeptide analog.

In preferred embodiments of the invention the foreign host in which the eucaryotic polypeptide analogs are produced is a bacterium.

The aminopeptidase enzyme used is preferably stable at a temperature up to about 65° C., and stable and active at neutral pH, i.e. about 7.0, and at an alkaline pH, i.e. from about pH 8.0 to about pH 10.0. The aminopeptidase is preferably of a molecular weight of less than about 100,000, and of bacterial origin. The enzyme can be an extracellular aminopeptidase. In specific embodiments an aminopeptidase which is insoluble in water may be used. The aminopeptidase may also be used while it is bound to a solid support, or may be removed at the end of the reaction by use of an affinity resin.

In a preferred embodiment of the invention the aminopeptidase is Aeromonas aminopeptidase. Other aminopeptidases may also be used, such as *Streptomyces griseus* aminopeptidase and *Bacillus stearothermophilus* aminopeptidase II or III.

The eucaryotic polypeptide analog may be a protein or any other peptide molecule such as apolipoprotein E, interferon, specifically gamma-interferon, or somatomedin, specifically somatomedin C. The polypeptide can also be a hormone, lymphokine, growth factor or derivatives thereof.

The N-terminal amino acid residue may be any amino acid. In specific embodiments of the invention the N-terminal amino acid residue is methionine or methionine followed by leucine. The N-terminal amino acid residue or a sequence of amino acid residues is bound to the N-terminal end of an amino acid residue or sequence of residues which acts as a stopping signal and stops the action of the aminopeptidase. In the embodiment in which Aeromonas aminopeptidase is used, the amino acid stopping signal may be an aspartic acid residue, a glutamic acid residue, or a sequence of residues comprising a residue other than proline bound to the N-terminal end of a proline residue. In a specific embodiment the amino acid stopping signal comprises a phenylalanine residue bound to the N-terminal end of a proline residue.

A specific embodiment of the invention involves the removal of N-terminal methionine residues from growth hormone analogs or derivatives thereof produced in bacteria. N-terminal methionine residues are removed from Met-hGH, Met-Asp-Gln-bGH, Met-bGH, and Met-pGH by contacting these growth hormone analogs with an aminopeptidase under suitable conditions permitting the removal of the N-terminal methionine residue.

Another embodiment of the invention involves the removal of both methionine and leucine residues from the N-terminal ends of growth hormone analogs or derivatives thereof produced in bacteria. An N-terminal methionine residue and its adjacent leucine residue are removed from Met-Leu-hGH by contacting this growth hormone analog with an aminopeptidase under suitable conditions permitting the removal of the two residues.

Another aspect of the invention is a method of adding N-terminal amino acid residues to a polypeptide molecule which comprises contacting the polypeptide molecule with an aminopeptidase and a sufficient excess of the free N-terminal amino acid to be added under suitable conditions permitting the addition of the amino acid to the N-terminus of the polypeptide. Aeromonas aminopeptidase is the preferred aminopeptidase for use in this embodiment of the invention.

In specific embodiments of the invention the Aeromonas aminopeptidase can be hyperactivated by metal substitutions of the coenzyme. In preferred embodiments Cu(II) is partially substituted for Zn(II) and Ni(II) is partially substituted for Zn(II).

The invention also concerns polypeptide analogs produced by the methods of the invention. Growth hormones and analogs of growth hormones such as human and bovine growth hormones have been produced according to the methods of the invention e.g. hGH, Asp-Gln-bGH and bGH.

Another aspect of the invention is a method of preparing analogs of eucaryotic polypeptide molecules which comprises producing a first analog in bacteria by expression of a gene encoding the analog of the eucaryotic polypeptide, removing the N-terminal methionine residue and its adjacent amino acid residue by the methods of the invention with an aminopeptidase and recovering the resulting analog. The recovery of the analog can be optimized by removing the N-terminal methionine residue and the adjacent amino acid residue that are removed by the aminopeptidase by use of ultrafiltration or dialysis.

DETAILED DESCRIPTION OF THE INVENTION

Figure 1:
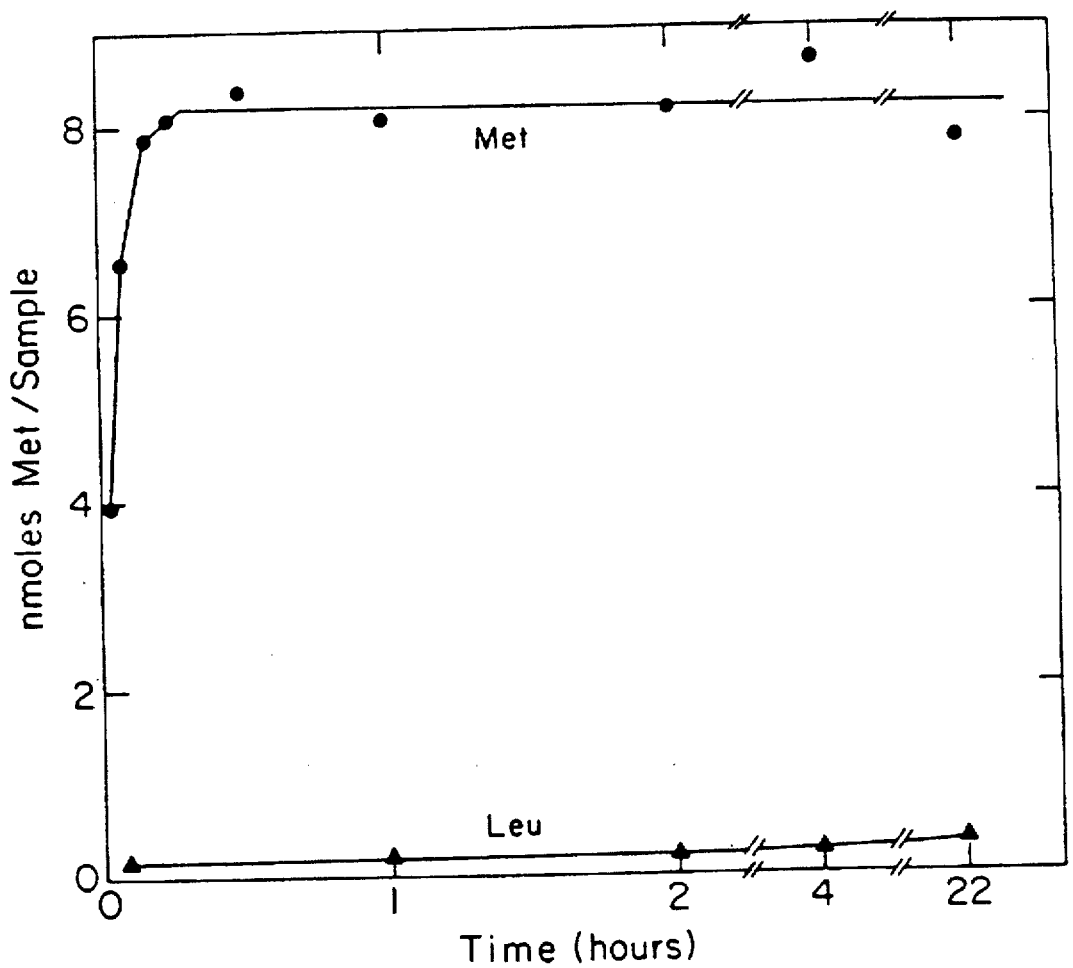
FIG. 1 shows the time course for the release of the N-terminal methionine from Met-hGH by *Aeromonas proteolytica* aminopeptidase as described in Example 1. By way of comparison, the release of leucine is also shown.

A method of sequentially removing one or more amino acid residues from the N-terminus of an analog of a eucaryotic polypeptide synthesized in a foreign host comprises contacting the eucaryotic polypeptide analog with an appropriate aminopeptidase under suitable conditions permitting sequential removal of N-terminal amino acid residues, the polypeptide analog containing an amino acid residue or sequence of residues located at a position other than the N-terminus of the polypeptide analog which stops the action of the aminopeptidase.

The foreign host in which the analog of the eucaryotic polypeptide is synthesized can be a bacterium or any other microorganism or organism which by use of recombinant DNA methods is capable of expressing a gene encoding for the analog and producing the resulting polypeptide.

The aminopeptidase is preferably an enzyme which remains stable at a temperature up to about 65° C. The aminopeptidase should also be stable and active at a neutral pH of about 7.0 and preferably at alkaline pH from about 8.0 to about 10.0.

In a preferred embodiment of the invention the aminopeptidase is of a molecular weight of less than about 100,000 and is of bacterial origin. The aminopeptidase can also be extracellular, insoluble in water or bound to a solid support such as agarose, or another polymeric substance. In specific embodiments of the invention an affinity resin may be used to remove excess aminopeptidase from the reaction mixture.

In the preferred embodiment of the invention the aminopeptidase is Aeromonas aminopeptidase. Other types of aminopeptidase may also be used, e.g. *Streptomyces griseus* aminopeptidase, *Bacillus stearothermophilus* aminopeptidase II or III.

Suitable conditions permitting the removal of the N-terminal amino acid residue are known to those of ordinary skill in the art and will vary according to the type of aminopeptidase used. In the case of Aeromonas aminopeptidase suitable conditions comprise an aqueous solution at alkaline pH of about 9.5 and a temperature of about 37° C.

The eucaryotic polypeptide analog may be any polypeptide or analog of a polypeptide, such as a hormone, lymphokine, or growth factor. Suitable eucaryotic polypeptides are apolipoprotein E, interferon, namely gamma-interferon, and somatomedin, namely somatomedin C. Specific embodiments of the invention concern removing N-terminal amino acids from analogs of eucaryotic growth hormones such as human, bovine, porcine, chicken or other animal growth hormones. In these embodiments an N-terminal methionine is added to the analogs of these polypeptide growth hormones when they are produced in bacteria by recombinant DNA methods. This invention provides a method of removing the N-terminal methionine and its adjacent amino acid from human, bovine, porcine and chicken growth hormone molecules or analogs of such molecules after they have been produced in bacteria.

In certain embodiments of the invention the amino acid residue or sequence of residues which stops the action of the aminopeptidase is located adjacent the N-terminal methionine. In this situation the aminopeptidase will remove the N-terminal methionine residue only.

In another embodiment of the invention the amino acid residue or sequence of residues which stops the action of the aminopeptidase is located adjacent the leucine in the molecule Met-Leu-hGH. In this situation, the aminopeptidase will remove both the N-terminal methionine residue and the leucine residue.

In other embodiments of the invention the residue or sequence of residues which stop the action of the aminopeptidase is separated from the N-terminal methionine by one or more amino acid residues. In this embodiment the aminopeptidase will also remove these other amino acid residues preceding the stopping signal, after it removes the N-terminal methionine.

In the case of Aeromonas aminopeptidase the amino acid residue which stops the action of the enzyme can be either aspartic acid or glutamic acid. In addition, a residue sequence comprising an amino acid other than proline bound to the N-terminus of a proline also functions as a stopping signal. In specific embodiments this stopping signal sequence comprises the amino acid phenylalanine bound to the N-terminal end of proline. This Phe-Pro sequence is the N-terminus of many natural animal growth hormone molecules. In a specific embodiment of the invention the N-terminal methionine is removed from animal growth hormone molecules produced by recombinant DNA methods in bacteria and which as a result of such production have a Met-Phe-Pro sequence at their N-terminus. In another embodiment of the invention the N-terminal methionine and its adjacent leucine residue are both removed from animal growth hormone molecules produced by recombinant DNA methods in bacteria and which as a result of such production have a Met-Leu-Phe-Pro sequence at their N terminus.

In specific embodiments of the invention the eucaryotic polypeptides are analogs of bovine growth hormone (bGH). These analogs contain the sequences Met-Asp-Gln or Met-Phe as their N-terminal sequence. The methionine is added to the N-terminus of these growth hormones when they are produced by recombinant DNA methods in bacteria. After removal of the N-terminal methionine by aminopeptidase, Asp-Gln-bGH and bGH are recovered respectively. The bGH used in this experiment was the phenylalanine form of bGH which has a phenylalanine residue as its N-terminus in its natural state. These methods also apply, however, to removal of N-terminal methionine from the terminus of the alanine form of bGH, which contains an alanine on the N-terminus of its natural form although in this case the alanine residue may also be removed.

A preferred embodiment of the invention concerns a method of removing the N-terminal methionine residue from a eucaryotic growth hormone analog such as animal and human growth hormone analogs, produced in bacteria by expression of a gene encoding the hormone which comprises contacting the growth hormone analog with Aeromonas aminopeptidase under suitable conditions permitting removal of the N-terminal methionine residue or the N-terminal methionine residue and its adjacent leucine residue.

A specific embodiment of the invention concerns a method of removing the N-terminal methionine residue from a human growth hormone (hGH) analog produced in bacteria by expression of a gene encoding the hormone, the human growth hormone analog having a methionine residue added to the N-terminus of authentic human growth hormone, which comprises contacting the analog with Aeromonas aminopeptidase under suitable conditions permitting the removal of the N-terminal methionine residue.

A specific embodiment of the invention concerns a method of removing the N-terminal methionine residue from a human growth hormone (hGH) analog produced in bacteria by expression of a gene encoding the hormone, the human growth hormone analog having a methionine residue added to the N-terminus of authentic human growth hormone, which comprises contacting the analog with Aeromonas aminopeptidase under suitable conditions permitting the removal of the N-terminal methionine residue.

Another specific embodiment of the invention concerns a method of removing the N-terminal methionine residue and its adjacent leucine residue from a human growth hormone (hGH) analog produced in bacteria by expression of a gene encoding the hormone, the human growth hormone analog having a methionine residue followed by a leucine residue added to the N-terminus of authentic human growth hormone, which comprises contacting the analog with Aeromonas aminopeptidase under suitable conditions permitting the removal of the N-terminal methionine residue and its adjacent leucine residue.

Another specific embodiment of the invention concerns a method of removing the N-terminal methionine residue from a bovine growth hormone analog produced in bacteria by expression of a gene encoding the bovine growth hormone analog, the bovine growth hormone analog having a methionine residue added to its N-terminus, which comprises contacting the analog with Aeromonas aminopeptidase under suitable conditions permitting the removal of the N-terminal methionine residue.

Another specific embodiment of the invention concerns a method of removing the N-terminal methionine residue from an interferon analog, such as gamma-interferon, produced in bacteria by expression of a gene encoding the interferon analog which comprises contacting the interferon analog with Aeromonas aminopeptidase under suitable conditions permitting removal of the N-terminal methionine residue.

Another specific embodiment of the invention concerns a method of removing the N-terminal methionine residue from a somatomedin analog, such as somatomedin C, produced in bacteria by expression of a gene encoding the somatomedin analog, the somatomedin analog having a methionine residue added to the N-terminus, which comprises contacting the analog with Aeromonas aminopeptidase under suitable conditions permitting the removal of the N-terminal methionine residue.

Another specific embodiment of the invention concerns a method of removing the N-terminal methionine residue from an apolipoprotein E analog produced in bacteria by expression of a gene encoding the analog, the analog having a methionine residue added to the N-terminus, which comprises contacting the analog with Aeromonas aminopeptidase under suitable conditions permitting the removal of the N-terminal methionine residue.

The invention also concerns a method of adding an N-terminal amino acid residue to a polypeptide molecule which comprises contacting the polypeptide molecule with an aminopeptidase and a sufficient excess of the free N-terminal amino acid residue to be added under suitable conditions permitting addition of the amino acid to the N-terminus of the polypeptide. Any aminopeptidase enzyme may be used; however, Aeromonas aminopeptidase is preferred. The aminopeptidase used will be able to add any amino acid residue to the N-terminus of the polypeptide as long as that amino acid does not function as a stopping signal for the enzyme and it would preferably add an amino acid to the N-terminus which serves as a stopping signal. Since the aminopeptidase reaction is a reversible reaction, the conditions for the addition reaction are the same as that of the cleavage reaction except for the concentration of the free amino acid to be added.

The activity of the Aeromonas aminopeptidase can be increased by metal substitutions. The greatest enhancement of activity occurs by partial or mixed metal substitutions essentially according to the methods J. M. Prescott et. al., Biochemical and Biophysical Research Communications, Vol. 114, No. (pp. 646–652) 2 (1983). The partial or mixed metal substitutions may be Cu(II) for Zn(II) or Ni(II) for Zn(II).

The invention also concerns polypeptide analogs produced by the methods of this invention such as human, bovine, porcine and chicken growth hormones or growth hormone analogs such as Asp-Gln-bGH.

Another aspect of the invention is a method of preparing an analog of a eucaryotic polypeptide which comprises providing a first analog in bacteria by expression of a gene encoding the analog of the eucaryotic polypeptide. The N-terminal methionine residue or an N-terminal methionine residue and its adjacent leucine residue of this analog is then removed by the method of this invention with an aminopeptidase, e.g. Aeromonas aminopeptidase. The resulting analog is then recovered by using methods known to those of ordinary skill in the art.

The recovery of the analog may be optimized by removing the free N-terminal methionine and leucine residues cleaved from the polypeptide analog by the aminopeptidase. Removal of the free amino acids drives the reaction to completion. The removal may be by any method known to those of ordinary skill in the art, e.g. ultrafiltration or dialysis. The invention also concerns analogs of eucaryotic polypeptides prepared by the methods of this invention such as growth hormones, e.g. human, bovine, and porcine growth hormone.

EXPERIMENTAL DETAILS

Materials and Methods

Met-hGH and Met-Asp-Gln-bGH were prepared by recombinant DNA techniques. Coomasie blue staining of polyacrylamide gels (15% gels) of the proteins, electrophoresed in the presence of sodium dodecyl sulfate and 2-mercaptoethanol reveals: a) a major band of Mw approximately 22,000 corresponding to Met-Asp-Gln-bGH and a very faint band with a slightly higher (lot 108-) (Bio-Technology General (Israel) Ltd.) or lower (lot 113D) (Bio-Technology General (Israel) Ltd.) molecular weight for the Met-Asp-Gln-bGH molecules; b) major band Mw approximately 22,000 and a very faint band with a slightly lower molecular weight for the Met-hGH (lot 1/100) molecule (Coomassie Blue). Scanning of S.D.S. gels reveals 88–93% purity for both proteins. Purity of 95% and greater has been obtained in other preparations. No detectable contaminating endopeptidase activity was present as judged by electrophoresis of the proteins on SDS-polyacrylamide gels after 24 hour incubation at 37° C.

Aeromonas aminopeptidase was prepared from the extracellular filtrate of *Aeromonas proteolytica* obtained from the American Type Culture Collection (ATCC 15338), essentially according to Prescott, J. M. and Wilkes, S. H., Methods Enzymol. 46: 530–543 (1976). The purification procedure included the following steps: sedimentation and filtration of bacteria, ammonium sulfate precipitation of the filtrate (367 g per liter), acetone fractionation (43.7% to 70% acetone), heat treatment at 70° C. (for 8 hrs.) to destroy endopeptidase activity, gel filtration on Sephadex G-75 and ion-exchange chromatography on DEAE-Sephadex A-50. In all experiments 10 mM Tris-HCl buffer, pH 8.0 replaced 10 mM tricine buffer, pH 8.0 employed by Prescott and Wilkes.

Preequilibration and elution from the G-75 column were performed in the presence of 5 micromoles $ZnCl_2$ rather than 50 micromoles $ZnCl_2$ employed in the original procedure. Purification on the DEAE-Sephadex A-50 column was performed by preequilibration of the column with 0.1M NaCl in 10 mM Tris-HCl, pH 8.0 containing 5 micromoles $ZnCl_2$, application of the sample and gradient elution with 0.6M NaCl in the same buffer (containing 5 micromoles $ZnCl_2$). After the salt concentration increased to about 0.5M the column was eluted with 0.7M NaCl in the same buffer. The major peak which Eluted from the column was collected and dialyzed against 10 nM Tris-HCl, 0.1M NaCl, pH 8.0 containing 5 micromolar $ZnCl_2$ and then kept frozen to $-20°$ C.

Prior to reaction with the growth hormones the enzyme solution was incubated at 70° for 2 hrs. to inactivate any possible traces of endopeptidase activity that might have been retained in the preparation and reactivated after prolonged storage. For large-scale experiments the enzyme was incubated at 70° C. for 3 h prior to reaction with the hormone.

Amino acid analysis was performed on a Dionex D-502 amino acid analyzer. Amino acid sequence analysis was carried out with an Applied Biosystems Gas Phase Sequencer followed by high performance liquid chromatography of the PTH-amino acids.

EXAMPLE I

Time Dependence of the Release of Free Methionine from Met-hGH by Aeromonas Aminopeptidase Prior to reaction with Met-hGH a sample of the aminopeptidase eluted from the DEAE-Sephadex A-50 column, 0.63 mg/ml in 10 mM Tris-HCl , 0.1M NaCl, pH 8.0, was incubated at 70° C. for 2 h to inactivate traces of endopeptidase activity. The enzyme was then diluted 3:1 with 2M Tris-HCl, pH 9.5 to a final concentration of 0.4725 mg/ml enzyme.

Met-hGH was dissolved to 8 mg/ml (by weight) in 10 mM Na Borate, pH 9.5.

Nine hundred microliters of Met-hGH solution and 19 microliters of the aminopeptidase solution were mixed and incubated at 37°. 50 microliter aliquots were taken after 2 min, 5 min, 10 min, 15 min, 30 min, 60 min, 2 h, 4 h and 22 h and precipitated by adding an equal volume of 3% sulfosalicylic acid solution in water, incubating at 37° for 15 min and then centrifuging in an Eppendorf bench centrifuge. 50 microliter samples of the supernatant were taken for direct amino acid analysis (without acid hydrolysis). Control experiments were run by precipitating Met-hGH solution (8 mg/ml) alone, directly after dissolution at time $t_o$ or after incubation of the Met-hGH alone at 37° for 4 h and for 22 h. Again for each of the controls 50 microliters of hormone solution was precipitated with an equal volume of 3% sulfosalicylic acid and 50 microliters of the supernatant were taken for amino acid analysis. Assuming a molecular weight of approximately 21,800 and that 85% of the weighed material is hormone (5%–10% water, 90%–95% purity of hormone), each analysis corresponds to 7.63 nmoles of Met-hGH starting material. The amount of methionine and several other amino acids liberated by the enzyme are listed in Table 1.

The release of methionine and that of leucine are depicted as a function of time in FIG. 1. The N-terminal sequence of Met-hGH is shown in Table IV. Polyacrylamide gel electrophoresis of the products reveals no detectable degradation of the hGH.

750 microliters of Met-Asp-Gln-bGH solution and 32 microliters of the aminopeptidase solution were mixed and incubated at 37°. 50 microliter aliquots were taken after 5 min, 10 min, 15 min, 30 min, 60 min, 2 h, 4 h and 22 h and precipitated by adding an equal volume of 3% sulfosalicylic acid solution in water, incubating at 37° C. for 15 min and centrifuging in an Eppendorf bench centrifuge. Again 50 microliter samples were taken for amino acid analysis. Control experiments were run by precipitating Met-Asp-Gln-bGH solution (8 mg/ml) alone either directly after dissolution at to or after incubation at 37° C for 22 h. Precipitation of protein and amino acid analysis of the supernatant were carried out as described in Example 1. Assuming a molecular weight of approximately 22,000 and that 85% of the weighed material is hormone (5–10% water, 90–95% purity of hormone), each analysis corresponds to

TABLE I

Analysis of Methionine and Some Other Amino Acids Released from the Digest of Met-hGH by Aeromonas Aminopeptidase (nmoles 50 microliter sample)

|     | 1<br>2 min | 2<br>5 min | 3<br>10 min | 4<br>15 min | 5<br>30 min | 6<br>60 min | 7<br>2 h | 8<br>4 h | 9<br>22 h | 10<br>Met-hGH<br>$t_o$ | 11<br>Met—HGH<br>4 h | 12<br>Met-hGH<br>22 h |
|-----|------|------|------|------|------|------|------|------|------|------|------|------|
| Met | 3.95 | 6.55 | 7.88 | 8.05 | 8.35 | 8.05 | 8.13 | 8.65 | 7.76 |      | less than 0.20 |      |
| Asp | 0.23 | 0.15 | 0.16 | 0.13 | 0.11 | 0.15 | 0.21 | 0.22 | 0.31 |      | less than 0.20 |      |
| Gly | 0.28 | 0.25 | 0.31 | 0.21 | 4.48* | 0.26 | 0.37 | 0.34 | 0.35 | 0.16 | 0.26 | 0.40 |
| Ala | 0.20 | 0.18 | 0.21 | 0.16 | 0.13 | 0.20 | 0.28 | 0.27 | 0.20 | 0.10 | 0.11 | 0.22 |
| Ile | 0.07 | 0.05 | 0.06 | 0.05 | 0.05 | 0.07 | 0.09 | 0.10 | 0.14 |      | less than 0.20 |      |
| Leu | 0.18 | 0.13 | 0.14 | 0.13 | 0.13 | 0.17 | 0.22 | 0.25 | 0.35 |      | less than 0.20 |      |
| Phe | less than 0.2 | | | | | | | | | | | |

*Most probably a contamination of the analysis sample
Neutral protease contaminants of aminopeptidase prefer to cleave internal peptide bonds on the amino side of hydrophobic amino acids. This reveals, for example, Leu and Ile residues which are then liberated by the aminopeptidases. The release of other amino acids not listed are also negligible.

EXAMPLE II

Time Dependence of the Release of Free Methionine from Met-Asp-Gln-bGH by Aeromonas Aminopeptidase Prior to reaction with Met-Asp-Gln-bGH a sample of the aminopeptidase eluted from the DEAE-Sephadex A-50 column was heated at 70° C. and diluted as described in Example I.

Met-Asp-Gln-bGH was dissolved to 8 mg/ml (by weight) in 10 mM Na Borate, pH 9.5.

7.41 nmoles Met-Asp-Gln-bGH starting material. The amount of methionine and several other amino acids liberated are listed in Table II.

Figure 2:
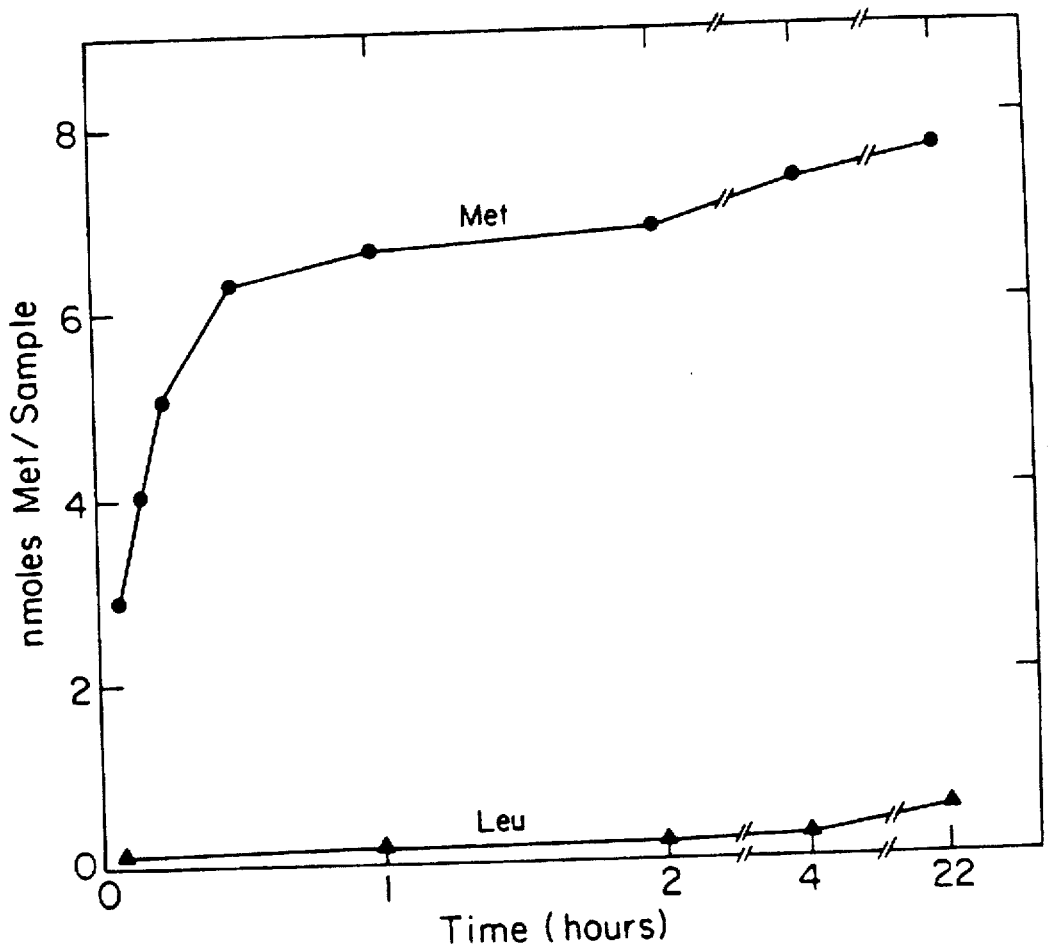
FIG. 2 shows the time course for the release of the N-terminal methionine from Met-Asp-Gln-bGH by *Aeromonas proteolytica* aminopeptidase as described in Example II. By way of comparison, the release of leucine is also shown.

The release of free methionine as well as of leucine as a function of time is depicted in FIG. 2. The N-terminus sequence Met-Asp-Gln-bGH is shown in Table IV.

Polyacrylamide gel electrophoresis of the products reveals no detectable degradation of bGH analog.

TABLE II

Analysis of Methionine and Some Other Amino Acids Released from the Digest of Met—Asp—Gln-bGF by Aeromonas Aminopeptidase (nmoles per 50 microliter sample)

|     | 1<br>5 min | 2<br>10 min | 3<br>15 min | 4<br>30 min | 5<br>60 min | 6<br>2 h | 7<br>4 h | 8<br>22 h | 9<br>Met—Asp—Gln-bGH<br>$t_o$ | 10<br>22 h |
|-----|------|------|------|------|------|------|------|------|------|------|
| Met | 2.87 | 4.06 | 5.04 | 6.28 | 6.63 | 6.81 | 7.33 | 7.69 | less than 0.20 | |
| Asp | 0.13 | 0.13 | 0.11 | 0.14 | 0.14 | 0.15 | 0.19 | 0.28 | less than 0.20 | |
| Gly | 0.16 | 0.19 | 0.15 | 0.27 | 0.19 | 0.19 | 0.19 | 0.26 | less than 0.20 | |
| Ala | 0.17 | 0.19 | 0.18 | 0.22 | 0.23 | 0.25 | 0.28 | 0.44 | less than 0.20 | |
| Ile | 0.05 | 0.06 | 0.06 | 0.07 | 0.07 | 0.09 | 0.10 | 0.21 | less than 0.20 | |

TABLE II-continued

Analysis of Methionine and Some Other Amino Acids
Released from the Digest of
Met—Asp—Gln-bGF by Aeromonas Aminopeptidase
(nmoles per 50 microliter sample)

|  | 1<br>5 min | 2<br>10<br>min | 3<br>15 min | 4<br>30 min | 5<br>60 min | 6<br>2 h | 7<br>4 h | 8<br>22 h | 9<br>Met—Asp—Gln-bGH<br>$t_o$ | 10<br><br>22 h |
|---|---|---|---|---|---|---|---|---|---|---|
| Leu | 0.10 | 0.11 | 0.12 | 0.15 | 0.18 | 0.22 | 0.27 | 0.56 | less than 0.20 | |
| Phe | less than 0.20 | | | | | | 0.12 | 0.28 | less than 0.20 | |

Neutral protease contaminants of aminopeptidases prefer to cleave internal peptide bonds on the amino side of hydrophobic amino acids. This reveals, for example, Leu and Ile residues which are then liberated by the aminopeptidases. The release of other amino acids not listed are also negligible.

EXAMPLE III

Comparison of Aeromonas Aminopeptidase and Leucine Aminopeptidase (Microsomal from Porcine Kidney, Sigma L5006)

Aeromonas aminopeptidase, 0.63 mg/ml in 10 mM Tris-HCl, 0.1 M NaCl, pH 8.0 was incubated at 70° C. for 2 h to inactivate traces of endopeptidase activity. The enzyme was then diluted 3:1 with 2M Tris-HCl, pH 9.5 to a final concentration of 0.4725 mg/ml.

Leucine aminopeptidase (porcine kidney, microsomal, Sigma L5006), 1 mg/ml suspension in 3.5M $(NH_4)_2 SO_4$, 10 mM $MgCl_2$, pH 7.7, 100 microliters was mixed with 0.5M Tris HCl, pH 9.5, 25 microliters $H_2O$, 150 microliters, and 0.025M $MnCl_2$, 25 microliters, and the mixture incubated at 37° C. for 2 h.

Met-hGH, was dissolved 11 mg/ml in 10 mM Na Borate, pH 9.5.

1) 290 microliters of Met-hGH solution, 11 mg/ml+microliters 10 mM Na Borate, pH 9.5+17 microliters Aeromonas aminopeptidase solution (final enzyme concentration: 19.3 micrograms/ml), or 2) 400 microliters of Met-hGH solution, 11 mg/ml+85 microliters leucine aminopeptidase activated enzyme+ 85 microliters 0.125M $MgCl_2$ (final incubated enzyme concentration: 49.7 micrograms/ml), were incubated at 37° C. and 75 microliter aliquots were taken after 5 min, 3h and 22 h and precipitated with an equal volume of 3% sulfosalicylic acid. After incubation at 37° C. for 15 min the mixture was centrifuged and 50 microliters of the supernatant were taken for direct amino acid analysis. Assuming a molecular weight of approximately 21,800 and that 85% of the weighed material is the hormone, each analysis corresponds to 7.46 nmoles and 7.53 nmoles Met-hGH of starting material for the reaction with the Aeromonas enzyme and the porcine leucine aminopeptidase, respectively.

Control experiments were run by precipitating Met-hGH with an equal volume of 3% sulfosalicylic acid after dissolution or after 22 h of incubation at 37° C. The precipitated mixture was incubated for 15 min at 37° C., centrifuged, and 50 microliters of the supernatant taken for direct amino acid analysis. The results of the experiment are given in Table III. These results show that the leucine aminopeptidase does not remove the N-terminal methionine and that the small amount of methionine released is likely due to the release from small peptides formed by contaminants of endopeptidase activity (see amounts of Ile and Leu). This conclusion is confirmed by polyacrylamide gel electrophoresis showing some degradation of the hormone by the enzyme after 22 h incubation at 37° C.

TABLE III

Release of N-Terminal Methionine from Met-hGH by Aeromonas
Aminopeptidase and by Porcine Kidney Leucine
Aminopeptidase (Microsomal) (nmoles/50 microliter sample)

|  |  | Met | Ile | Leu |
|---|---|---|---|---|
| Met-hGH at $t_o$ (1) | | less than 0.1 | | |
| Met-hGH 22 h at 37° C. (2) | | less than 0.1 | | |
| Met-hGH + Aeromonas Amino-peptidase | 5 min (1) | 6.76 | less than 0.1 | |
| Met-hGH + Aeromonas Amino-peptidase | 3 h (2) | 7.11 | 0.09 | 0.19 |
| Met-hGH + Aeromonas Amino-peptidase | 22 h (3) | 7.27 | 0.10 | 0.28 |
| Met-hGh + Leucine Aminopeptidase | 5 min (1) | less than 0.1 | | |
| Met-hGH + Leucine Aminopeptidase | 3 h (2) | 0.25 | 0.09 | 0.27 |
| Met-hGH + Leucine Aminopeptidase | 22 h (3) | 0.62 | 0.78 | 1.12 |

Neutral protease contaminants of aminopeptidases prefer to cleave internal peptide bonds on the amino side of hydrophobic amino acids. This reveals for example Leu and Ile residues which are then liberated by the aminopeptidases.

EXAMPLE IV

Removal of N-terminal Methionine from Met-Asp-Gln-bGH and Preparation of the Sample for Sequence Analysis 2.5 ml Met-Asp-Gln-bGH, 8 mg/ml in 10 mN Na Borate, pH 9.5, was incubated with 106 microliters enzyme, 0.4725 mg/ml in 0.5M Tris-HCl, pH 9.5, 22 h at 37° C. For the determination of the amino terminal sequence, 2 ml of the mixture were diluted 1:1 with 10 mM Na Borate, pH 9.5 and 1 ml 15% sulfosalicylic acid were added, the mixture incubated at 37° C. for 15 min and precipitated by centrifugation. The pellet was resuspended in 5 ml 3% sulfosalicylic acid and recentrifuged. The pellet was suspended in 5 ml 10 mM Na Borate, pH 10.5 and dialyzed against three 2 liter changes of water containing 1 ml, 0.3 ml and 1 ml of concentrated ammonium hydroxide, respectively, and then was dialyzed against water. The sample was brought to 20% acetic acid (by glacial acetic acid) and used for sequence analysis. The results of the sequence analysis, shown in Table IV, demonstrate that more than 95% of the molecules have the N-terminal sequence Asp-Gln-Phe-Pro.

TABLE IV

N-Terminal Sequences of Growth Hormone Derivatives Before and After Removal of N-Terminal Methionine by Aeromonas Aminopeptidase

| Growth Hormone Derivative | N-terminal Sequence[4] | N-terminus (%)[5] |
|---|---|---|
| 1) Met—Asp—Gln—bGH[1] | Met—Asp—Gln—Phe—Pro | Met (90–100)[6] |
| 2) Asp—Gln—bGH[2] | Asp—Gln—Phe—Pro | Asp (95)[7] |
| 3) Met—hGH[1] | Met—Phe—Pro | Met (90–100)[6] |
| 4) hGH[3] | Phe—Pro | Phe (99)[7] |

[1] Bovine growth hormone analog.
[2] Obtained from derivative (1) in example IV.
[3] Obtained from derivative (3) as described in example V.
[4] Amino acid sequence analysis was carried out with an Applied Biosystems Gas Phase Sequencer followed by high performance liquid chromatography of the PTH-amino acids.
[5] Determined by sequence analysis.
[6] The amount of methionine at the N-terminus of the starting products was estimated by the amount of free methionine liberated by reaction with the Aeromonas aminopeptidase after precipitation with sulfosalycilic acid and analysing the supernatant by amino acid analysis.
[7] The amino acid present at the N-terminus of the products was estimated from PTH-amino acid analysis of the 1st cycle of the sequence analysis.

EXAMPLE V

Use of Ultrafiltration or Dialysis to Drive the Reactions

The reactions carried out by the enzyme are reversible. Thus, removal of one of the products will tend to further drive the reaction to completion. We have demonstrated this by removing the liberated methionine residue during the course of the reaction, thus driving the reaction to further produce hGH. The liberated methionine residue was eliminated by ultrafiltration.

Twelve grams of Met-hGH in 1500 ml, 10 mM Na Borate, pH 9.5, was incubated with 12.4 ml of enzyme 0.4725 mg/ml in 0.5M Tris-HCl, pH 9.5, at 37° C. for 2 h. An additional amount of 6.2 ml of the same enzyme solution was added and incubation at 37° C. was continued for 3½ h. The solution was placed for ultrafiltration and about 50 liters of 10 mM NaBorate, pH 9.5, were passed through the material during 4 h to remove free methionine and drive the enzymatic reaction to completion. Incubation at 37° C. was then continued for 12½ h. Total duration of the incubation and ultrafiltration was 22 h. The material was absorbed on DEAE-Sephacel and the resin washed with 10 mM NaBorate, pH 9.0 and then with 10 mM NaBorate, pH 9.0 containing 25 mM NaCl, 50 mM NaCl and 75 mM NaCl. The hormone was eluted with 10 mM NaBorate, pH 9.0, containing 100 mM NaCl. The eluted hormone was concentrated, and dialyzed by ultrafiltration and lyophilized. A sample was dissolved in 20% acetic acid and subjected to sequence analysis. The results of analysis are shown in Table IV. The results demonstrate that in more than 99% of the molecules, the N-terminal methionine was removed and there was no further degradation of the protein.

EXAMPLE VI

Time Dependence of the Release of Free Methionine and Free Leucine from Met-Leu-hGH by Aeromonas Aminopeptidase Prior to reaction with Met-Leu-hGH, a sample of the aminopeptidase eluted from the DEAE-Sephadex A-50 column was heated at 70° C. and diluted as described in Example I.

Met-Leu-hGH was dissolved to 8 mg/ml (by weight) in 10 mM Na Borate buffer, pH 9.0. The pH was raised to 10.6, then dropped to 8.8, and finally the mixture was centrifuged to remove a small amount of precipitate. The supernatant solution was used for reaction.

One thousand microliters of the Met-Leu-hGH solution and 21 microliters of the Aeromonas aminopeptidase were mixed and incubated at 37°. Seventy-five microliter aliquots were taken after 2 min., 5 min., 10 min., 30 min., 60 min., 2 h. and 22 h. and precipitated by adding an equal volume of 3% sulfosalicylic acid solution in water, incubating at 37° for 15 min. and then centrifuging in an Eppendorf bench centrifuge. Fifty microliter samples of the supernatant were taken for direct amino acid analysis (without acid hydrolysis). Control experiments were run by precipitating the Met-Leu-hGH solution (8 mg/ml) alone with an equal volume of 3% sulfosalicylic acid, at a time $t_o$ or after incubating the Met-Leu-hGH solution at 37° for 22 h. Again 50 microliters of the supernatant solutions were taken for direct amino acid analysis. The results of this experiment are summarized in Table V.

The N-terminal sequence of Met-hGH is shown in Table IV. Polyacrylamide gel electrophoresis of the products reveals no detectable degradation of the hGH.

TABLE V

Analysis of Methionine and Leucine As Well as Some Other Amino Acids Released from the Digest of Met—Leu-hGH by Aeromonas Aminopeptidase (nmoles per 50 microliter sample)

| | 1<br>2 min | 2<br>5 min | 3<br>10 min | 4<br>15 min* | 5<br>30 min | 6<br>60 min | 7<br>2 h | 8<br>22 h | 9<br>$t_o$ | 10<br>22 h |
|---|---|---|---|---|---|---|---|---|---|---|
| Met | 5.15 | 4.85 | 4.83 | 2.94 | 5.28 | 5.30 | 4.85 | 4.70 | less than 0.2 | 0.32 |
| Leu | 4.80 | 4.58 | 4.47 | 2.73 | 5.10 | 5.22 | 4.71 | 5.52 | less than 0.2 | 0.10 |
| Asp | less than 0.2 | | | | | | | | 0.2 | less than 0.2 |
| Gly | less than 0.2 | | | | | | | | | |
| Ala | less than 0.2 | | | | | | | | 0.23 | 0.2 |
| Ile | less than 0.2 | | | | | | | | | |
| Phe | less than 0.2 | | | | | | | | | |

*Most probably a pipetting error. The release of other amino acids not listed is also negligible.

EXAMPLE VII

Removal of Met from a Commercial Preparation of Met Gamma-Interferon.

Thirty microliters of gamma-interferon (Amgen; Interferon-gamma-4A; ARN 3010, batch 1), containing the authentic sequence of the lymphokine and having a specific activity of $1-5\times10^7$ units/mg, was subjected to microsequence analysis. Analysis of the first three amino acids indicated that the material contains Met-gamma-Interferon with the N-terminal sequence Met-Gln-Asp (with some trace of Arg found in the third cycle).

This gamma-interfer-on derivative was acted upon by the Aeromonas aminopeptidase and found to release free methionine as determined by amino acid analysis using a particularly sensitive amino acid analyzer with picomole sensitivity and ortho-phthalaldehyde post-column derivatization. Note that all other amino acid analyses in the application were carried out at nanomole sensitivities using a Dionex D-502 amino acid analyzer. All sequence analyses were carried out on an Applied Biosystems Model 470A protein sequencer and followed by HPLC of the PTH-amino acids. The procedure of the removal of the methionine is as follows:

Methionyl-gamma-interferon: Interferon-gamma$_{4A}$ ARN 3010, batch 1, $10^7$ units/ml ($1-5\times10^7$ units/mg) in 0.04M Tris.HCl, ph 7.0.

Aeromonas aminopeptidase: (Lot 2), 0.5 mg/ml in 0.1M NaCl-10 mM Tris-HCl 5 micromoles $ZnCl_2$, ph 8.0 was heated at 70° for 2 h, prior to use. It was then diluted 1:9 with 0.1 m NaCl, 10 nM Tris·HCL, 5 micromolar $ZnSO_4$, pH 8.0, to 0.05 mg/ml enzyme.

Procedure: 12 microliters of the gamma-interferon solution and 3 microliters of the enzyme solution (0.05 mg/l) were incubated at 37° C. for 35 min and the mixture cooled on ice. After 30 min, 14 microliters of the mixture were dried by lyophilization and loaded on the amino acid analysis column without further treatment. Control experiments were run by incubating 12 microliters of the gamma-interferon alone and 3 microliters of the enzyme alone, at 37° C. for 35 min, drying the samples as above and applying them on the amino acid analysis column.

The amount of methionine released was 96 picomoles and the background of other amino acids was fairly normal: Asp, 15 picomoles; Thr, 24 picomoles; Ser, 39 picomoles; Glu, 8 picomoles; Gly, 53 picomoles; Ala, 23 picomoles; Val, 10 picomoles; Leu, 8 picomoles and Phe, 11 picomoles; there was another large contaminating peak, at the position where the enzyme reference also showed a peak. Relatively large background peaks of Ser and Gly were also seen on the gamma-interferon reference. Assuming that the specific activity of the sample is $5\times10^7$ units/mg and mol wt. for gamma-interferon of approximately 17,000, the amount of methionine released amounts to 73% of the theoretical value. If the specific activity of the material is lower than the above assured value, percentage of removal of Met could be lower.

This experiment indicates that the N-terminal methionine can be selectively and efficiently removed from Met-gamma-interferon by Aeromonas aminopeptidase.

EXAMPLE VIII

Removal of an N-Terminal Met from an Interferon

A recombinant interferon analog having a Met at its N-terminus was processed according to the method of the present invention. Met was selectively removed from the N-terminus of the molecule by the Aeromonas aminopeptidase.

EXAMPLE IX

Removal of an N-Terminal Met from a Somatomedin C Polypeptide

A recombinant somatomedin C polypeptide having a Met at its N-terminus was processed according to the method of the present invention. Met was selectively removed from the N-terminus of the molecule by the Aeromonas aminopeptidase.

EXAMPLE X

Removal of Met from Met-Porcine Growth Hormone (PGH) and Non-Removal of N-Terminal Ala from the Mature Recombinant $Cu_2$—$Zn_2$ Human Superoxide Dismutase.

Aeromonas aminopeptidase lot 2, 0.5 mg/ml (in 0.1M NaCl-10 mM Tris HCl pH 8.0 was heated at 70° C. for 2 hours prior to use, then diluted 3:1 with 2M Tris HCl, pH 9.5.

Met-PGH (lot 5/100) and $Cu_2$—$Zn_2$ human superoxide dismutase (SOD lot 1) were prepared by recombinant techniques. The latter has the authentic N-terminal sequence of the mature protein except that the N-terminal Ala is not N-Acetylated.

Procedure: The proteins were dissolved, 8 mg/ml in 10 mM sodium borate, pH 9.5. To 600 microliters of the protein solutions were added 34 microliters of the enzyme solution and the mixtures were incubated at 37° C. Samples were taken with time and precipitated with equal volume of 3% sulfosalicylic acid and incubated at 37° C. for 15 minutes, then centrifuged. 50 microliters of the supernatant solutions were taken for amino acid analysis. Control experiments were run by incubating the proteins alone at 37° C. for 22 h and proceeding with the amino acid analyses as above. Assuming 85% content of the weighed proteins and molecular weights of 22,000 and 16,000 (per subunit) for Met-PGH and $Cu_2$—$Zn_2$ superoxide dismutase, respectively, the theoretical amount of N-terminal residues in each analysis are 7.31 nmoles and 10.17 nmoles, respectively. The amount of Met and Ala released are shown in Table VI.

TABLE VI

Release of Met from Met—PGH and Ala from recombinant $Cu_2$—$Zn_2$ human superoxide dismutase by Aeromonas aminopeptidase*

|  | 30 min | 3 hr | 22 hr | t22 hr (control) |
|---|---|---|---|---|
| Met—PGH |  |  |  |  |
| Met released Recombinant | 1.95 | 2.41 | 4.63 | 0.11 |
| $Cu_2$—$Zn_2$ human superoxide dismutase Ala released | .15 | .32 | .53 | 0.10 |

*Under the same conditions, the release of Met from Met-hGH was essentially quantitative in 3 hours.

There could be several reasons for the non-stoichiometric removal of Met from Met-PGH (in contrast to the stoichiometric removal of Met from Met-hGH). One explanation could be that the molecules could be present as non-covalently associated dimers and that the N-terminal methionine of only one of the molecules in the dimer is accessible to the enzyme attack, whereas the N-terminal methionine of the other molecule in the dimer is sterically hindered. For this reason, only about 50%–60% of the N-terminal methionine residues were removed. Met-hGh, on the other hand, is monomeric. Another possibility is that in Met-pGH part of the molecules are still formulated and the enzyme does not remove formyl-methionine. In order to prove any of these or other possibilities further experiments would be required.

EXAMPLE XI

Removal of Met, Lys and Val from Apolipoprotein E by Aeromonas Aminopeptidase Methionyl-Apolipoprotein E (Lot CC 017) with the N-terminal sequence Met-Lys-Val-Glu was prepared in *E. coli* and purified. It was used as a solution of 2.53 mg/ml in 5 mM $NH_4HCO_3$.

Aminopeptidase. Aeromonas aminopeptidase (Lot 2) was used in the experiment. The enzyme, 0.5 mg/ml in 0.1M NaCl, 10 mM Tris-HCl-5 micromolar $ZnCl_2$, pH 8.0 was heated for 2.5 hours prior to reaction with the protein.

Procedure. 600 microliters of Methionyl-Apolipoprotein E and 12.25 microliters of enzyme were incubated at 37° C. and 90 microliter aliquots of the mixture were taken with time and precipitated with 10 microliters of 15% sulfosalycilic acid in water. The mixture was incubated at 37° C. for 15 minutes and centrifuged. 50 microliters of the supernatant were taken for direct amino acid analysis (without acid hydrolysis). A control experiment was run by incubating the protein alone without the enzyme for 22 hours, and proceeding with the analysis as above. The amounts of methionine, lysine and valine released from the protein are given in Table VII.

TABLE VII

Release of Met, Lys and Val from Methionyl-Apolipoprotein E by Aeromonas Aminopeptidase
(nmoles amino acid released)

|     | 10 min | 30 min | 1 h  | 4 h  | 22 h | $t_{22}$ (control) |
|-----|--------|--------|------|------|------|--------------------|
| Met | 2.64   | 2.77   | 2.73 | 2.88 | 3.09 | less than 0.1      |
| Lys | 2.11   | 2.37   | 2.44 | 2.64 | 2.80 | "                  |
| Val | 1.87   | 2.19   | 2.10 | 2.41 | 3.22 | "                  |

The amount of methionine, lysine and valine released agree with the theoretical amount expected, based on the specified concentration of the sample and assuming a molecular weight of approximately 35,000 for the protein (i.e. 3.19 nmoles each). Yet, the removal of the third amino acid, Val is somewhat slower than the other amino acids. Within the first 1 hour of reaction no release of Glutamic acid could be observed indicating the stopping character of this amino acid for the aminopeptidase. After 22 hours of incubation, a small amount of degradation of the protein could be observed on polyacrylamide gel electrophoresis in the presence of sodium dodecyl sulfate (SDS) and 2-mercaptoethanol. This could reflect traces of endopeptidase activity in either the substrate or the enzyme. The SDS gels show that the new ApoE derivative, without the three amino acids Met, Lys, and Val, migrates slightly faster than the parent protein. Interestingly, the enzyme in the reaction mixture lost activity after incubation for 22 hours, probably caused by the Apolipoprotein E which is cytotoxic and may also inactivate the enzyme. With all other substrates tested so far, the enzyme activity in the reaction mixture is fairly well preserved after 22 hours at 37°.

EXAMPLE XII

Removal of Met from Met-bGH

This example shows the removal of N-terminal methionine from Methionyl-bGH, where bGH is the phenylalanine form of bGH, having the N-terminal sequence Met-Phe-Pro.

Met-bGH (Lot 178) was prepared in *E. coli* for the purpose of the present experiments.

Aminopeptidase. Aeromonas aminopeptidase (Lot 2), 0.5 mg/ml in 0.1M NaCl-10 mM Tris-HCl, 5 micromolar $ZnCl_2$, pH 8.0 was preheated at 70° C. for 2 h prior to use, then diluted 3:1 with 2M Tris HCl, pH 9.5 to a final concentration of 0.375 mg/ml.

Procedure The hormone was suspended, 8 mg/ml, in 10 mM sodium borate buffer, pH 9.5, the pH was raised to 12 with 1N NaOH, then lowered back to pH 9.4 with 1N HCl, then centrifuged to remove a slight amount of precipitate, and yielded a solution of approximately 7 mg/ml.

One thousand microliters of the Met-bGH solution and 56.3 microliters of the enzyme solution were incubated at 37° C. and 75 microliter aliquots of the mixture were taken with time and precipitated with an equal volume of 3% sulfoalycilic acid. After incubation of the mixture at 37° C. for 15 min, the precipitate was centrifuged and 50 microliters of the supernatant taken for direct amino acid analysis (without acid hydrolysis). Control experiments were run by precipitating the hormone alone at time zero or after incubation at 37° C. for 22 h and proceeding with the analyses as above. The results of the experiment are given in Table VIII.

TABLE VIII

Release of Met from Methionyl-bGH by Aeromonas Aminopeptidase
(nmoles Met/50 µl sample)

| 2 min | 5 min | 10 min | 30 min | 1 h  | 2 h  | 4 h  | 22 h | $t_0$ | $t_{22}$ Control |
|-------|-------|--------|--------|------|------|------|------|-------|------------------|
| 3.48  | 3.67  | 3.76   | 3.77   | 3.77 | 3.81 | 4.19 | 4.45 | 0.1   | 0.29             |

The experiment demonstrates that the reaction of Aeromonas aminopeptidase with Met-bGH is very rapid since at 20 micrograms/ml of enzyme most of the reaction is complete in 2 min.

The stoichiometries of the reaction is about 65% as opposed to stoichiometry of 90–100% which were observed for the reaction of the enzyme in several reactions with two different batches of Met-hGh, with Met-Asp-Gln-bGH and with Met-Apolipoprotein E as well as with Met-gamma-interferon and Met-somatomedin. On the other hand, reaction with Met-Leu-hGH and Met-bGH showed only approximately 65% of Met released/mole substrate and with Met-pGH only approximately 50%–60%. We have recently observed that with certain new batches of Met-Asp-Gln-bGH the stoichiometry is also in the 50–60% range. We previously assumed that this partial stoichiometry would be due to either a) not completely pure materials; b) incomplete removal of the N-formyl group by the *E. coli* host deformylating enzyme(s) and/or; c) to dimer formation of some hormones and accessibility of the enzyme to only one of the monomers in the dimer. We found indications for yet another likely explanation for the incomplete stoichiometry, namely, that the host *E. coli* processing enzyme system partially removes some of the N-terminal methionine, e.g. in Met-pGH and Met-bGH, before purification of the proteins.

EXAMPLE XIII

Biological Activity of Authentic Recombinant hGH, Obtained from Met-hGH by Removal of Met with Aeromonas Aminopeptidase The authentic recombinant hGH obtained from Met-hGH by reaction with Aeromonas aminopeptidase by procedures essentially the same as those described in Examples I and V including use of ultrafiltration to remove free methionine is biologically active and displays high activity. Thus, the batch preparation of hGH described in Example 1 and 2 (lot 2/100), that was derived from Met-hGH lot 1/100 has an N-terminal Phe. Its immunoreactivity is the same as that of pituitary hormone from frozen glands and its biological activity by radioreceptor binding assay is 2.1 IU/mg. In addition, another batch preparation of Met-hGH (lot 4.1.1) that was passed on an anion-exchange column to remove deamidated forms of the hormone, then treated with the Aeromonas aminopeptidase, using the ultrafiltration techniques to remove free methionine that was released during the reaction in order to drive the reaction to completion, then passed on another column of an anion exchanger and lyophilized, was designated lot 4.2.1 and analyzed. The results were:

a) The first 38 amino acids for N-terminus were identical to that of the natural pituitary derived product, with the amino acid at the N-terminus being Phe (at least 99%).

b) The C-terminal residue was Phe, also identical to that of the pituitary derived product.

c) The immunoreactivity is 1.35 times higher than that of a commercial preparation from pituitary.

d) The activity by radio-receptor binding assay is 2.5 units/mg protein.

Discussion

The experiments and results presented above clearly demonstrate that Aeromonas aminopeptidase rapidly removes the N-terminal methionyl residue from Met-hGH, Met-Asp-Gln-bGH, Met-gamma-interferon, Met-Somatomedin C, Met-pGH, Met-Apolipoprotein E, and Met-bGH molecules prepared by recombinant DNA techniques. Also, the aminopeptidase can remove the N-terminal methionine residue and its adjacent leucine residue from Met-Leu-hGH, prepared by recombinant DNA techniques. Precautions taken to avoid endopeptidase activity both from the substrate and the aminopeptidase have proven successful in the sense that the enzymatic reactions contain very little if any detectable endopeptidase cleavages (FIGS. 1 and 2 and Tables I-VIII) even after 22 h of incubation of the hormones with the aminopeptidase. Thus, conditions under which completion of the enzymatic reaction takes place without significant endopeptidase activity are readily available.

Additionally, the results of Example VI demonstrate that Aeromonas aminopeptidase can rapidly remove several amino acids from eucaryotic polypeptide analogs, not only one methionyl residue. In particular, it has been demonstrated that the N-terminal methionyl and leucyl residues can be removed from Met-Leu-hGH to yield authentic human growth hormone.

The most striking conclusion of the experiment of Example VI is that the amount of methionine and leucine released is the same, even after only two minutes of reaction. This is due to the fact that the leucine residue is probably being removed at a faster rate than the methionine residue. Thus, a recombinant DNA product of the design Met-Leu-hGH, where Met is followed by Leu, assures that the final product will be hGH with no detectable presence of Leu-hGH molecules.

This experiment demonstrates that the authentic molecule can be obtained not only from a methionyl-derivative but also from a methionyl-x-derivative where x is another amino acid. Similarly, an authentic molecule would be obtained from $(x)_n$-derivative where n is greater than two.

The enzymatic reaction is specific. In the two reactions examined, there are clear Asp and X-Pro stops of the aminopeptidase that are in accord with the specificity of the enzyme towards small peptides.

The reactions studied are quantitative. Confirmation of this conclusion was partly achieved by preliminary sequence analysis where at least 99% and 95% of the N-terminal residues of the products of reaction of the aminopeptidase and the hormones were found to be Phe and Asp for the human and bovine growth hormone products, respectively. Confirmation of the quantitative aspect of the reaction is confronted with obvious handicaps of the sequencing method (sensitivity, noise, by-products and separation limits) and the actual figures could be even higher than those given above.

It should be noted in this regard that the enzymatic reaction Met-Protein⇌Met+Protein is reversible and it could in principle be driven to synthesis by adding excess methionine or to complete hydrolysis by continuous removal of the amino acid. In one of the examples (Example V) demonstrating a batch preparation of hGH we have indeed employed ultrafiltration for several hours at a progressive stage of the reaction to remove free methionine and assist completion of the reaction.

Removal of the aminopeptidase from the reacted hormone is achieved by selective absorption and desorption of the hormone to an anion-exchange resin. Other alternative ways to remove the aminopeptidase after its reaction with the hormone could be the use of a water-insoluble derivative of the enzyme in a batch or packed in a column as well as the use of an affinity resin for the enzyme to absorb it at the end of the reaction.

The procedure used for Met-hGH, Met-Asp-Gln-bGH, Met-Leu-hGH, Met-gamma-interferon, Met-somatomedin C, Met-pGH, Met-apolipoprotein E, and Met-bGH should be applicable to other growth hormones and polypeptides. Methods for obtaining the aminopeptidase can be improved (e.g. more economical process of isolation or genetically engineering the enzyme or developing microorganism overproducing aminopeptidase and endopeptidase-free mutants of the microorganism). Other aminopeptidases of low molecular weight (less than 100,000) like *Streptomyces griseus* aminopeptidase and aminopeptidases which are thermostable and active at alkaline pH could possibly substitute for the Aeromonas enzyme.

In addition to its action on growth hormones the aminopeptidase(s) can be useful for other recombinant DNA products such as hormones, growth factors, and enzymes that possess N-terminal sequences in accordance with the specificity of the enzyme or enzymes, e.g. somatomedins, interleukin 3, interferons, apolipoprotein E. Furthermore, the recombinant DNA products can be designed in a manner which would allow the removal of several amino acids from the N-terminus, in addition to the methionine residue. For example derivatives like Met-Lys-bGH, Met-Leu-Tyr-bGH and Met-Phe-Asp-Gln-bGH when acted upon by aminopeptidase will yield hGH, bGH, bGH and Asp-Gln-bGH, respectively. It may be also possible to use the enzyme to add an amino acid by using excess of the amino acid in the incubation mixture, thus driving the synthesis reaction.

What is claimed is:

1. A method of removing N-terminal methionyl group from recombinant methionyl human growth hormone produced so as to obtain human growth hormone having the biological activity of naturally-occurring human growth hormone which comprises contacting the recombinant methionyl human growth hormone with Aeromonas aminopeptidase under conditions such that the N-terminal methionyl group is removed and recovering the resulting human growth hormone.

2. A method of claim 1, wherein the contacting is at a pH from about 8.0 to about 10.0.

3. A method of removing N-terminal methionyl group from a recombinant eucaryotic methionyl polypeptide produced so as to obtain a polypeptide having the biological activity of the naturally-occurring polypeptide which comprises contacting the recombinant methionyl polypeptide with Aeromonas aminopeptidase under conditions such that the N-terminal methionyl group is removed and recovering the resulting polypeptide.

* * * * *